United States Patent [19]

Nair et al.

[11] 4,021,544
[45] May 3, 1977

[54] COMPLEMENT INHIBITORS

[75] Inventors: Vijay Gopalan Nair, Nanuet, N.Y.; Joseph Peter Joseph, Cliffside Park, N.J.; Seymour Bernstein, New City, N.Y.

[73] Assignee: American Cyanamid Company, Stamford, Conn.

[22] Filed: July 12, 1976

[21] Appl. No.: 704,584

[52] U.S. Cl. .................................. 424/180; 536/4; 536/118

[51] Int. Cl.$^2$ .......................................... A61K 31/70

[58] Field of Search ................ 424/180; 536/4, 118

[56] References Cited

UNITED STATES PATENTS 3,911,915  11/1975  Seifter .............................. 424/180

*Primary Examiner*—Lewis Gotts
*Assistant Examiner*—Cary Owens
*Attorney, Agent, or Firm*—Jack W. Richards

[57] ABSTRACT

Sulfated oligosaccharides of the maltose series useful as complement inhibitors.

6 Claims, No Drawings

COMPLEMENT INHIBITORS

BACKGROUND OF THE INVENTION

The present invention resides in the concept of sulfated oligosaccharides of the maltose series having the 1α → 4α configuration and their use as inhibitors of the complement system of warm-blooded animals.

Oligosaccharides of the maltose series have been isolated and characterized, *J. Amer. Chem. Soc.*, 71: 356 (1949); *J. Amer. Chem. Soc.*, 72: 677 (1950); *J. Amer. Chem. Soc.*, 76: 1671 (1954); *Analytical Chemistry*, 26: 1514 (1955). *J. Chem. Soc.* 3692 (1958); and *Analytical Chemistry*, 34: 1736 (1962). Partial sulfation products of maltose, as well as, lactose, sucrose, mannnotriose and stachyose are known, *J. Pharm. Soc.* Japan, 87: 1052 (1967). Sulfuric esters of maltose oligosaccharides have been prepared and their anti-coagulant activity investigated, *Chemistry and Industry*, October, 982 (1952).

U.S. Pat. Nos. 2,686,779 and 2,697,093 disclose a method of preparing the alkali metal sulfates of polysaccharides, such as, cellulose, starch, inulin and dextrin, and U.S. Pat. No. 3,271,388, the preparation of the alkali metal and ammonium salts of amylopectin sulfates useful as anti-coagulants. *British J. Pharmocol,.* 7: 370 (1952) discloses sulfuric acid esters of starch and *Acta. Physiologica Scand.*, 8: 215 (1944); 9: 28 (1945); 9: 35 (1945); and 110 211 (1946), sulfuric acid esters of starch having anticoagulant and platelet agglutination activity. A sulfated polyglucose is known to posses anticoagulant activity, *Lab. Invest.* 13 (8), 865 (1964). Certain sulfated polysaccharides are disclosed as having anti-inflammatory action, e.g., dextrin sulfate, pentosan polysulfate and amylopectin sulfate, *Biochemical Pharmacology*, 18: 1285 (1969). The sulphated polysaccharide heparin is known to have anti-complement activity, e.g., *J. Infect. Dis.*, 44: 250 (1929). Pentosan polysulfo ester and dextran sulfate are also said to possess anti-complementary action, *Pharmacology*, 9: 74–79 (1973); *Z. Naturforsch*, 266: 403 (1971); *Chemical Abstracts*, 52: 485h (1958); *Fed. Proc.* 140 157 (1955); and 75: 33179s (1971). Phlorizin (a compound containing glucose) is known to possess anti-complement activity *Biochemical Pharmacology*, 23: 3107 (1974).

The term complement refers to a complex group of proteins in body fluids that, working together with antibodies or other factors, play an important role as mediators of immune, allergic, immunochemical and-/or immunopathological reactions. The reactions in which complement participates takes place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated Clq, Clr and Cls. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39, 935–938 (1968); *Scientific American*, 229, (No. 5), 54–66 (1973); *Medical World News*, October 11, 1974, pp. 53–58; 64–66; *Harvey Lectures*, 66, 75–104 (1972); *The New England Journal of Medicine*, 287, 489–495; 545–549; 592–596; 642–646 (1972); *The Johns Hopkins Med. J.*, 128, 57–74 (1971); and *Federation Proceedings*, 32, 134–137 (1973).

The complement system can be considered to consist of three sub-systems: (1) a recognition unit (Clq) which enables it to combine with antibody molecules that have detected a foreign invader; (2) an activation unit (Clr, Cls, C2, C4, C3), which prepares a site on the neighboring membrane; and, (3) an attack unit (C5, C6, C7, C8 and C9) which creates a hole in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunipathological process. The nature of certain of the complement proteins, suggestions regarding the mode of complement binding to biological membranes and the manner in which complement effects membrane damage are discussed in *Annual Review in Biochemistry*, 38, 389 (1969).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New England Journal of Medicine*, 286, 808–812 (1972); *Allergol, Et. Immunipath*, II, 163–168 (1974); *J. Allergy Clin. Immunol.*, 53, No. 5, 298–302 (1974); and *Annals of Internal Medicine*, 84, 580–593 (1976).

SUMMARY OF THE INVENTION

It has now been discovered that certain sulfated oligosaccharides of the maltose series having the $1\alpha \rightarrow 4\alpha$ configuration interact with the complement reaction sequence, thereby inhibiting complement activity in body fluids.

This invention is particularly concerned with the pharmaceutically acceptable poly(H-)sulfate and salts of oligosaccharides of the maltose series having the $1\alpha \rightarrow 4\alpha$ configuration and the following formula:

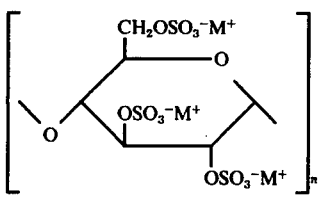

wherein M represents hydrogen or the salt, as hereinafter defined, and $n$ is 2–10. Operable pharmaceutically acceptable salts encompassed within this invention include the salts of alkali metals, alkaline earth metals, ammonium and amines selected from triloweralkylamine ($C_1$–$C_6$), piperidine, pyrazine, alkanolamine ($C_1$–$C_6$), and cycloalkanolamine ($C_1$–$C_6$).

Representative compounds of the present invention, include, for example, the following: maltose poly(H-)sulfate trimethylamine salt; maltose poly(H-)sulfate sodium salt; maltotriose poly(U-)sulfate trimethylamine salt; maltotriose poly(H-)sulfate sodium salt; maltotetraose poly(H-)sulfate trimethylamine salt; maltotetraose poly(H-)sulfate sodium salt; maltopentaose poly(H-)sulfate trimethylamine salt; maltopentaose poly(H-)sulfate sodium salt; maltohexaose poly(H-)sulfate trimethylamine salt; maltohexaose poly(H-)sulfate sodium salt; maltoheptaose poly(H-)sulfate trimethylamine salt; maltoheptaose poly(H-)sulfate sodium salt; maltooctaose poly(H-)sulfate trimethylamine salt; maltooctaose poly(H-)sulfate sodium salt; maltononaose poly(H-)sulfate trimethylamine salt; maltononaose poly(H-)sulfate sodium salt; maltodecaose poly(H-)sulfate trimethylamine salt and maltodecaose poly(H-)sulfate sodium salt.

The sulfated oligasaccharides of the maltose series, having the $1\alpha \rightarrow 4\alpha$ configuration encompassed within this invention may be prepared by the application or adaptation of known methods, for example, as described in *Chemical Reviews*, 62: 549–589 (1962), and U.S. Pat. No. 2,686,779, 2,697,093, 2,923,704 or 3,271,388. For example, they may be prepared by dissolving or suspending the corresponding oligosaccharide in an organic solvent such as dimethylformamide at 20°–100° C. To this is added the salt forming substituent such as trimethylamine sulfur, trioxide and the mixture is stirred and heated at 20°–100° C. for 8–24 hours. The additon of an organic solvent such as ethanol causes the precipitation of the poly(H-)sulfate salt which is collected by conventional methods and may be further purified by reprecipitation from organic solvents such as ethanol or ether, e.g., *Chemical Reviews* ibid. the alkali or alkaline earth metal salts may be prepared by dissolving the above trialkylamine salts in water, adding aqueous alkali acetate and charcoal and filtering through diatomaceous earth. The filtrate is poured into ethanol causing precipitation of the poly(H-)sulfate alkali salt. This salt is again dissolved in water, alkali acetate is added and the salt is again precipitated from ethanol.

This invention is concerned with a method of inhibiting the complement system in a body fluid, such as blood serum, which comprises subjecting said body fluid complement to the action of an effective complement inhibiting amount of a poly(H-)sulfate salt of an oligosaccharide of the maltose series. Body fluid can include blood, plasma, serum, synovial fluid cerebrospinal fluid, or pathological accumultions of fluid as pleural effusion, etc.

The method of use aspect of this invention is also concerned with a method of inhibiting the complement system in a warm-blooded animal which comprises internally administering to said animal an effective complement inhibiting amount of a poly(H-)sulfate salt of an oligosaccharide of the maltose series.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary angioneurotic edema and inflammatory states induced by the action of bacterial or lysosomal enzymes on the appropriate complement components as for example, inflammation following coronary occlusion. They may also be useful in the treatment of transplant rejection and as blood culture and transport mediums.

DETAILED DESCRIPTION OF THE INVENTION

The following examples describe in detail the preparation and formulation of representative compounds of the present invention.

EXAMPLE 1

Maltose Poly(H-)Sulfate Trimethylamine Salt

A 1.0g portion of D-maltose is suspended in 30 ml of dimethylformamide. A 3.9 g portion of trimethylamine-sulfur trioxide is added and the mixture is stirred at 60°–70° C. overnight. The excess dimethylformamide is decanted and the resulting orange gum is triturated twice with fresh dimethylformamide then two more times with absolute ethyl alcohol. The solid is collected, washed with absolute ethanol and anhydrous ethyl ether and dried in vacuo over phosphorpus at room temperature for 18 hours to give 3.43 g of white solid.

EXAMPLE 2

Maltose Poly (H-)Sulfate Sodium Salt

A 3.0 g portion of maltose poly(H-)sulfate trimethylamine (prepared as in Example 1) is dissolved in 10 ml of water plus 5.0 ml of 30% aqueous sodium acetate solution. The solution is filtered through diatomaceous earth and the filtrate is poured with stirring into 100 ml of ethyl alcohol producing a white solid which is collected by filtration. The treatment with sodium acetate and ethanol is repeated and the reprecipitated solid is collected and dried to yield 2.23 g. of the product of the Example.

EXAMPLE 3

Meltotriose Poly(H-)sulfate Trimethylamine Salt

A 1.0 g. portion of maltotriose is suspended in 10 ml. of dimethylformamide. A 2.01 g. portion of trimethylamine sulfur trioxide is added and the mixture is stirred at 60°–70° C. overnight. Absolute alcohol is added and a white gummy solid separates. The solid is collected and triturated twice with absolute ethanol. The solid is mixed with ethanol and ether and stirred overnight. The solid is collected, washed with ethanol and ether and dried giving 2.47 g. of white hygroscopic solid.

EXAMPLE 4

Maltotriose Poly(H-)sulfate Sodium Salt

To 10 ml. of eater containing 4 ml. of 30% aqueous sodium acetate is added 2.0 g. of maltotriose poly(H-)sulfate trimethylamine sulfate. When solution is complete charcoal is added and the mixture is filtered through diatomaceous earth. The filtrate is poured with stirring into 100 ml. of ethanol producing a white gum. Two repetitions of treatment with sodium acetate, charcoal and ethanol produces 344 mg. of white solid.

EXAMPLE 5

Maltotetraose Poly(H-)Sulfate Trimethylamine Salt

A portion of maltotetraose is suspended in dimethylformamide and the required amount of trimethylamine-sulfur trioxide is added. The procedure described in Example 3 is followed and the product of the Example is collected, washed and dried.

EXAMPLE 6

Maltotetraose Poly(H-)Sulfate Sodium Salt

A portion of maltotetraose poly(H-)sulfate trimethylamine sulfate is added to a volume of water containing an aliquot of 30% aqueous sodium acetate. The procedure is continued as described in Example 4 resulting in the product of the example.

EXAMPLE 7

Maltopentaose Poly(H-)Sulfate Trimethylamine Salt

A portion of maltopentaose is suspended in dimethylformamide and the required amount of trimethylamine-sulfur trioxide is added. The procedure described in Example 3 is followed and the product of the Example is collected, washed and dried.

EXAMPLE 8

Maltopentaose Poly(H-)Sulfate Sodium Salt

A portion of maltopentaose poly(H-)sulfate trimethylamine sulfate is added to a volume of water containing an aliquot of 30% aqueous sodium acetate. The procedure is continued as described in Example 4 resulting in the product of the Example.

EXAMPLE 9

Maltohexaose Poly(H-)Sulfate Trimethylamine Salt

A portion of maltohexaose is suspended in dimethylformamide and the required amount of trimethylamine-sulfur trioxide is added. The procedure described in Example 3 is collected, washed and dried.

EXAMPLE 10

Maltohexaose Poly(H-)sulfate Sodium Salt

A portion of maltohexaose poly(H-)sulfate trimethylamine sulfate is added to a volume of water containing an aliquot of 30% aqueous sodium acetate. The procedure is continued as described in Example 4 resulting in the product of the example.

EXAMPLE 11

Maltoheptaose Poly(H-)sulfate Trimethylamine Salt

A 1.0 g portion of maltoheptaose (amyloheptaose) [Journal of the American Chemical Society, 71, 356 (1949)] is dissolved in 10 ml of dimethylformamide by heating in an oil-bath at 60°–70° C. When solution is complete, 3.33 g of trimethylamine sulfur trioxide is added and the mixture is stirred at 60°–70 C for 20 hours with formation of a solid. The mixture is cooled and the dimethylformamide is decanted, the solid is triturated again with fresh dimethylformamide then twice with absolute ethyl alcohol and finally with absolute ether to give 3.03 g. of tan solid.

EXAMPLE 12

Maltoheptaose Poly(H:)sulfate Sodium Salt

A 1.0 g portion of maltoheptaose poly(H-)sulfate trimethylamine sulfate is dissolved in 10 ml of water. Then 5 ml of 30% aqueous sodium salt acetate solution is added and the mixture is poured into 60 ml of alcohol with stirring. A mixture of gum and solid is collected after stirring ½ hour. the material is redissolved in 5 ml of water and 2.5 ml of 30% aqueous sodium acetate solution and is poured with stirring into 100 ml of alcohol resulting in separation of a white finely dispersed solid. The solid is collected by filtration, washed twice with alcohol, followed by anhydrous ether and is dried in vacuo at room temperature over phosphorous pentachloride to give 750 mg of the product of the Example.

EXAMPLE 13

Maltooctaose Poly(H-)sulfate Trimethylamine Salt

A portion of maltooctaose is dissolved in dimethylformamide and is reacted with trimethylamine-surfur trioxide according to the procedure described in Example 11.

EXAMPLE 14

Maltooctaose Poly(H-)sulfate Sodium Salt

A portion of maltooctaose poly(H-)sulfate trimethylamine sulfate is added to a volume of water containing an aliquot of 30% aqueous sodium acetate. The procedure is continued as described in Example 12 to give the product of the Example.

EXAMPLE 15

Maltononaose Poly(H-)sulfate Trimethylamine Salt

A portion of maltononaose is dissolved in demethylformamide and is reacted with trimethylamine-sulfur trioxide as described in the procedure of Example 11.

EXAMPLE 16

Maltononaose Poly(H-)sulfate Sodium Salt

A portion of maltononaose poly(H-)sulfate trimethylamine sulfate is added to a volume of water containing an aliquot of 30% aqueous sodium acetate. The procedure is continued as described in Example 12 to yield the product of the Example.

EXAMPLE 17

Maltodecaose Poly(H-)sulfate Trimethylamine Salt

A portion of maltodecaose is dissolved in dimethylformamide and is reacted with trimethylamine sulfur trioxide as described in the procedure of Example 11.

EXAMPLE 18

Maltodecaose Poly(H-)sulfate Sodium Salt

A portion of maltodecaose poly(H-)sulfate trimethylamine sulfate is added to a volume of water containing an aliquot of 30% aqueous sodium acetate. The procedure is continued as described in Example 12 to yield the product of the Example.

EXAMPLE 19

| Preparation of Compressed Tablet | mg./tablet |
|---|---|
| Active Ingredient | 0.5–500 |
| Dibasic Calcium Phosphate NF | qs |
| Starch USP | 40 |
| Modified Starch | 10 |
| Magnesium Stearate USP | 1–5 |

EXAMPLE 20

| Preparation of Compressed Tablet-Sustained Action | mg./tablet |
|---|---|
| Active Ingredient as Aluminum Lake*, Micronized | 0.5–500 as acid equivalent |
| Dibasic Calcium Phosphate NF | qs |
| Alginic Acid | 20 |
| Starch | 35 |
| Magnesium Stearate USP | 1–10 |

*Complement inhibitor as sodium salt with Al$_2$(SO$_4$)$_3$ yields complement inhibitor aluminum salt with Na$_2$SO$_4$. Complement inhibitor content in Aluminum Lake ranges from 5–30%.

EXAMPLE 21

| Preparation of Hard Shell Capsule | mg./capsule |
|---|---|
| Active Ingredient | 0.5–500 |
| Lactose, Spray Dried | qs |
| Magnesium Stearate | 1–10 |

EXAMPLE 22

| Preparation of Oral Liquid (Syrup) | % W/V |
|---|---|
| Active Ingredient | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 23

| Preparation of Oral Liquid (Elixir) | % W/V |
|---|---|
| Active Ingredient | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 24

| Preparation of Oral Suspension (Syrup) | % W/V |
|---|---|
| Active Ingredient as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 25

| Preparation of Injectable Solution | % W/V |
|---|---|
| Active Ingredient | 0.05–5 |
| Benzyl Alcohol N.F. | 0.9 |
| Water for Injection qs ad | 100.0 |

EXAMPLE 26

| Preparation of Injectable Oil | % W/V |
|---|---|
| Active Ingredient | 0.05–5 |
| Benzyl Alcohol | 1.5 |
| Sesame Oil qs ad | 100.0 |

EXAMPLE 27

| Preparation of Injectable Depo-Suspension | % W/V |
|---|---|
| Active Ingredient as Aluminum Lake, Micronized | 0.05–5 (acid equivalent) |
| Polysorbate 80 USP | 0.2 |
| Polyethylene Glycol 4000 USP | 3.0 |
| Sodium Chlorode USP | 0.8 |
| Benzyl Alcohol N.F. | 0.9 |

Example 27-continued

| Preparation of Injectable Depo-Suspension | |
|---|---|
| | % W/V |
| HCl to pH 6–8 | qs |
| Water for Injection qs ad | 100.0 |

EXAMPLE 28

| Preparation of Intra-articular Composition | |
|---|---|
| Active Ingredient (micronized) | 2–20 mg. |
| NaCl (physiological saline) | 0.9% |
| Benzyl Alcohol | 0.9% |
| Sodium Carboxymethylcellulose | 1–5% |
| pH Adjusted to 5.0–7.5 | |
| Water for Injection qs ad | 100% |

The compounds of this invention may be administered internally, e.g., orally or parenterally, e.g., intra articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg./kg./day, or every six hours for more rapidly excreted salts, may be used. For intra-articular use for large joints such as the knee, from about 2 to about 20 mg./joint per week may be used, with proportionally smaller doses for smaller joins. The dosage range is to be adjusted to provide optimum therapeutic response in the warm-blooded animal being treated. In general, the amount of compound administered can vary over a wide range to provide from about 5mg./Kg. to about 100 mg./kg. of body weight of animal per day. The usual daily dosage for a 70kg. subject may vary from about 350 mg. to about 3.5 g. Unit doses of the salt can contain from about 0.5 mg. to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e. oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs nd similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are inidcated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor) - This test measures the ability of activated human C1 to destroy fluid phase human C2 in the presence of C4 and appropriate dilutions of the test compound. An active inhibitor protects C2 from C1 and C4; (ii) Test, Code 035 (C3–C9 inhibitor) - This test determines the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor) - In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test - Here, the well known complement dependent lesion, Forssman vasculitis, is produced in guinea pigs by intradermal injection of rabbit anti-forssman antiserum. The lesion is measured in terms of diameter, edema and hemorrhage and the extent to which a combined index of these is inhibited by prior intraperitoneal injection of the test compound at 200 mg/kg in then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction Test — In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

Some of the compounds of the present invention have been found to possess anti-coagulant activity as well as complement inhibiting activity. The in vitro anti-coagulant activity (AC) of the compounds of this invention has been demonstrated by the following test:

The computation of an *Intrinsic Therapeutic Index* (ITI) was devised to correlate the results expressed in wells, obtained in the in vitro Code 026 (C1 inhibitor) test and the in vitro anti-coagulant (AC) test into a meaningful value which would aid in the net evaluation of the activity of the compounds of this invention.

The ITI of a given compound may be defined as the antilogarithm of the logarithmic (base 2) difference between the highest serial dilution in wells which is active in the Code 026 test and the highest serial dilution in wells providing activity in the anti-coagulant test. The ITI is thus a measure of the separation of anti-complement and anti-coagulant acitivities; the higher the numerical value the more therapeutically useful the separation of activities.

The *Intrinsic Therapeutic Index* of the compounds of this invention are listed in Table II.

TABLE II

| Compound | INTRINSIC THERAPEUTIC INDEX IN VITRO ACTIVITY | | LOGARITHMIC DIFFERENCE EXPRESSED AS WELLS | INTRINSIC THERAPEUTICAL INDEX |
|---|---|---|---|---|
| | COMPLEMENT INHIBITING ACTIVITY (WELLS) CODE 026 | ANTI-COAGULANT ACTIVITY (WELLS) AC | | |
| Maltose Poly(H—) sulfate trimethylamine salt | +8 | −2 | +10 | 1024 |
| Maltose Poly(H—) sulfate sodium salt | +12 | +2 | +10 | 1024 |
| Maltotriose Poly(H—) sulfate trimethylamine salt +7 | −1 | +8 | 256 | |
| Maltotriose Poly(H—) sulfate sodium salt | +9 | −1 | +10 | 1024 |
| Malto Heptaose Poly(H—) sulfate trimethylamine salt | +9 | +4 | +5 | 32 |
| Malto Heptaose Poly(H—) sulfate sodium salt | +9 | +4 | +5 | 32 |

Citrated sheep plasma (CSP) is added to various dilutions of test compound in a Microtiter plate, the CSP sample mixture are then recalcified with an isotonic sheep red blood cell (RBC) suspension. The sheep RBC'S, kept in suspension throughout the clotting incubation time, become enmeshed in the fibrin matrix if a clot forms. Upon centrifugation of the plate untrapped RBC's form buttons, the sizes of which correspond to the degree of clot inhibition; this providing a measure of anti-coagulant activity (AC). Sodium heparin is used as a positive control and activity is reported in wells, appearing in Table 1.

With reference to Table I, the results of tests, Code 026, 035, 036 and Cap 50 show that the compounds of the invention prossess complement inhibiting activity.

We claim:
1. A method of inhibiting the complement system in a body fluid which comprises subjecting said body fluid to the action of an effective complement inhibiting amount of a compound selected from those of the formula:

TABLE I

| Compound | BIOLOGICAL ACTIVITIES IN VITRO ACTIVITY | | | | |
|---|---|---|---|---|---|
| | 026* Wells | 035* Wells | 036* Wells | A.C.* Wells | Cap 50* |
| Maltose Poly(H—) sulfate trimethylamine salt | +8** | Neg. | Neg. | −2 | 500 |
| | +10 | Neg. | Neg. | | 500 |
| Maltose Poly(H—) sulfate sodium salt | +12 | Neg. | Neg. | +2 | 500 |
| | +11 | Neg. | Neg. | | 500 |
| Maltotriose Poly(H—) sulfate trimethylamine salt | +7 | Neg. | Neg. | −1 | 500 |
| Maltotriose Poly(H—) sulfate sodium salt | +9 | Neg. | Neg. | −1 | 500 |
| Maltoheptaose Poly(H—) sulfate trimethylamine salt | +9 | 3 | 5 | +4 | 168 |
| | +9 | 5 | 5 | | 134 |
| Maltoheptaose Poly(H—) sulfate sodium salt | +8 | 4 | 6 | +4 | 98 |
| | +9 | 5 | 6 | +4 | 86 |
| | +9 | +4 | 5 | | 100 |

*Code Designation for tests employed as referred to herein.
**Activity in wells a serial silution assay. Higher well number indicates higher activity. The serial dilutions are two-fold.

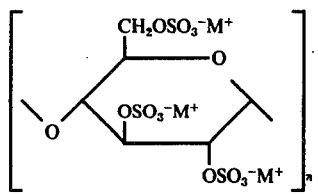

wherein M represents hydrogen or the salt of an alkali metal, alkaline earth metal, ammonia, triloweralkylamine ($C_1$–$C_6$), piperidine, pyrazine, alkanolamine ($C_1$–$C_6$); and cycloalkanolamine ($C_1$–$C_6$); and $n$ is 2–10.

2. A method according to claim 1 wherein $n$ is 2–10 and M is selected from the group comprising trimethylamine and sodium.

3. A method according to claim 1 wherein the body fluid is blood serum.

4. A method of inhibiting the complement system in a warm-blooded animal which comprises internally administering to said animal an effective complement inhibiting amount of a compound selected from those of the formual:

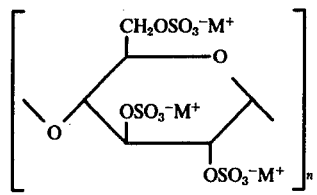

wherein M represents hydrogen or the salt of an alkali metal, alkaline earth metal, ammonia, triloweralkylamine ($C_1$–$C_6$), piperidine, pyrazine, alkanolamine ($C_1$–$C_6$); and cycloalkanolamine ($C_1$–$C_6$); and $n$ is 2–10.

5. A method according to claim 4 wherein the compound is administered intra-articularly.

6. A method according to claim 4 wherein $n$ is 2–10 and M is selected from the group comprising trimethylamine and sodium.

* * * * *

UNITED STATES PATENT OFFICE
CERTIFICATE OF CORRECTION

Patent No. 4021544  Dated May 3, 1977

Inventor(s) Vijay Gopalan Nair, Joseph Peter Joseph and Seymour Bernstein

It is certified that error appears in the above-identified patent and that said Letters Patent are hereby corrected as shown below:

Column 13, line 14,

Change "cycloalkanolamine ($C_1-C_6$)" to --cycloalkanolamine ($C_3-C_6$)--.

Column 14, line 2,

Change "formual" to --formula--

Column 14, line 16,

Change "cycloalkanolamine ($C_1-C_6$)" to --cycloalkanolamine ($C_3-C_6$)--.

Signed and Sealed this sixteenth Day of August 1977

[SEAL]

Attest:

RUTH C. MASON
*Attesting Officer*

C. MARSHALL DANN
*Commissioner of Patents and Trademarks*